United States Patent
Burton et al.

(10) Patent No.: US 6,513,528 B2
(45) Date of Patent: Feb. 4, 2003

(54) METHOD AND DEVICE FOR VAS OCCLUSION

(76) Inventors: John Burton, 15460 Wing Lake Dr., Minnetonka, MN (US) 55441; Ricky James Ferraro, 9104 E. 109th Ave., Crown Point, IN (US) 46307; Jerome Socha, 501 6th St., Newport, MN (US) 55055; Greg Townsend, 3402 Pilgrim La. N., Plymouth, MN (US) 55441

( * ) Notice: Subject to any disclaimer, the term of this patent is extended or adjusted under 35 U.S.C. 154(b) by 0 days.

(21) Appl. No.: 09/990,526

(22) Filed: Nov. 21, 2001

(65) Prior Publication Data

US 2002/0059936 A1 May 23, 2002

Related U.S. Application Data

(63) Continuation-in-part of application No. 09/718,550, filed on Nov. 22, 2000.

(51) Int. Cl.$^7$ .................................................. A61F 6/02
(52) U.S. Cl. ...................................... 128/842; 128/843
(58) Field of Search .............................. 128/842, 830, 128/843, 833, 844, 918; 604/96

(56) References Cited

U.S. PATENT DOCUMENTS

| | | | | |
|---|---|---|---|---|
| 3,687,129 A | * | 8/1972 | Nuwayser | 128/843 |
| 4,308,859 A | * | 1/1982 | Child | 128/833 |
| 4,351,326 A | * | 9/1982 | Kosonen | 128/833 |
| 6,042,563 A | * | 3/2000 | Morejohn | 604/96 |

* cited by examiner

Primary Examiner—Michael A. Brown
(74) Attorney, Agent, or Firm—Beck & Tysver, P.L.L.C.

(57) ABSTRACT

A pair of removable soft pliant plugs is inserted in the Vas to impede the flow of sperm to provide reversible male contraception.

15 Claims, 4 Drawing Sheets

METHOD AND DEVICE FOR VAS OCCLUSION

This is a continuation in part of application Ser. No. 09/718,550, filed Nov. 22, 2000.

FIELD OF THE INVENTION

The present invention relates generally to male contraception and more generally to devices and methods for reversibly occluding the vas deferens of a male.

BACKGROUND OF THE INVENTION

Sterilization is the most popular method of contraception in the United States among couples with children and no desire for more children. It is believed that the acceptance of male contraception would improve if the procedure were more likely to be reversible. At present the surgical reversal of a vasectomy is problematic and requires microsurgery.

Various techniques have been applied to occlude the vas to achieve reversible contraception. For example, exterior clips have been used to "squeeze off" the lumen of the vas. However, it has been found that the pressure levels required for reliable occlusion promotes tissue necrosis. Injectable plugs have been used to "fill" the vas. However the delivery of the filler material is difficult and the curing time lengthens the procedure time. These "formed-in-place" plugs have also proved prone to migration which is undesirable.

The use of an inserted plug for vas occlusion is known from U.S. Pat. No. 4,512,342. The patent disclosed a pair of plugs, which are inserted through two closely, placed incisions in the vas. The plugs are tethered together and a portion of the tether is external to the vas lumen. The plugs are inserted with the aid of a stylus.

Published literature describes the evolution of the device and both single and double plugs were explored during development. Various anchor techniques and "no anchors" were tried. This design process resulted in the product described in the patent. Although the device is safe and effective there is a continuing need to improve both the implanted device and the methods and apparatus used to implant the device.

SUMMARY

According to the preferred methods of the invention, a pair of plugs called intra vas devices (IVD) are inserted through one or two holes in the vas. Each IVD has a hollow tubular body with a blunt and sealed end. A delivery device is provided to stretch the plug to both extend its length and to reduce its diameter. Although it is difficult to quantify, it is important to note that the IVD is very stretchable and flexible. A mandrel like core or stylus called a "stylet" extends through the IVD to engage the blunt end of the IVD. A release feature on the stylet device allows the physician to release the tension on the IVD plug to deploy the plug once it is positioned in the vas. One version of the stylet delivery device has a set of spring loaded jaws which engage the IVD plug at its proximal end. The release feature releases the jaws so the plug may assume a "relaxed" shape in the vas. Another version of the device uses tension on tether to stretch the IVD.

A sizer/dilator is used to both dilate the vas and to measure the internal diameter of the vas. Although this sizer step is optional it is preferred as an aid to selecting the correct diameter of plug. In operation, the optimal procedure sequence is to exteriorize the vas using a conventional surgical approach. Then, while holding the vas outside the scrotum a small puncture, incision or "nick" is made in the vas to create a surgical opening. Next the size/dilator is introduced to measure and dilate the lumen of the vas. With this information at hand the physician can select the appropriately sized IVD to load onto a stylet delivery device.

BRIEF DESCRIPTION OF THE DRAWINGS

Through the several views of the drawing illustrative versions of the devices are shown. In the drawing identical reference numerals indicate identical structures wherein.

DETAILED DESCRIPTION

Figure 1:
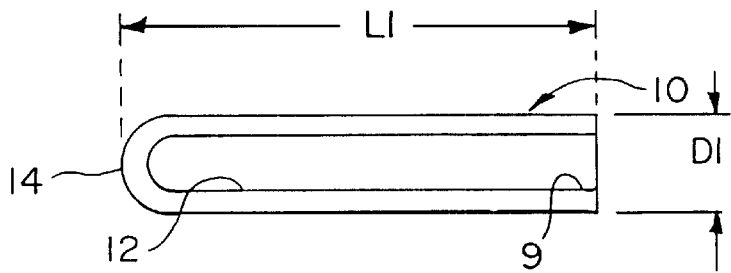
FIG. 1 is a cross section of an IVD.

FIG. 1 shows an exemplary vas occlusion plug or IVD that forms a part of the invention. The IVD plug 10 is hollow as indicated by interior lumen 12. The IVD is made from a soft pliant biocompatible material such as a low durometer, high elongation silicone rubber. High elongation silicone rubber with durometer measure of 30 has been effective in experiments and in clinical trials. The IVD 10 is formed with a closed and blunt distal end 14. The proximal end 9 is open. When the IVD is molded and in its unstretched state it has a characteristic length L1 and a characteristic diameter D1 which are labeled in the figure. In general the IVD will be offered in various sizes (D1) and lengths (L1) with up to six representative sizes presently contemplated as; 1.0 mm, 1.2 mm, 1.4 mm, 1.6 mm, 1.8 mm and 2.0 mm.

Figure 2:
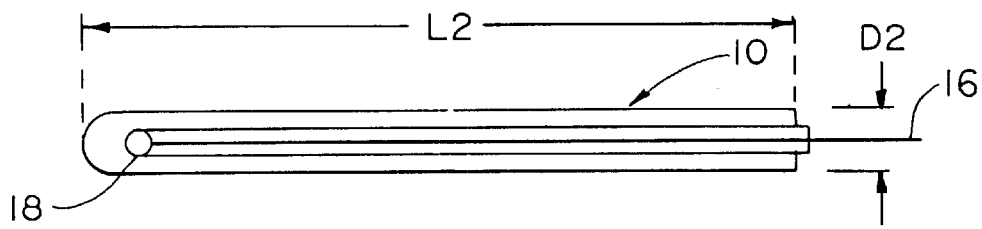
FIG. 2 is a cross section of an IVD.

FIG. 2 shows the IVD of FIG. 1 stretched to its insertion length L2 which corresponds to a diameter reduction to a dimension shown as D2 in the figure. To maximize the reduction in diameter for a given amount of stretch a material with a high Poisson ratio is desirable. The IVD is stretched by the application of traction between the interior distal tip and the proximal outer surface. The force is applied to the distal tip through insertion of a stylet 16 that forms a part of the delivery device. This stylet 16 should be blunt. This bluntness is accentuated in the figure by the ball end 18 forming the distal tip of the stylet16.

Figure 3:
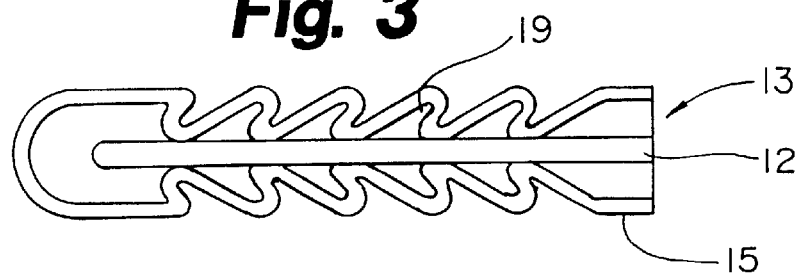
FIG. 3 is a cross section of an IVD.

FIG. 3 shows an externally "ribbed" IVD 13 that has an optional metalic coating 15 of copper or other spermicidal material. The bulk material is silicone rubber and mirrors the construction of the IVD 10. However the ribs typified by rib 19 increase the path length of the IVD so that sperm is less likely to travel over the entire length of the IVD and the sperm that does pass over the IVD has greater contact with the metal layer. It is also anticipated that the ribbed portion may allow for a broader range of fit of IVD to the vas and prevent migration of the IVD within the vas.

Figure 15:
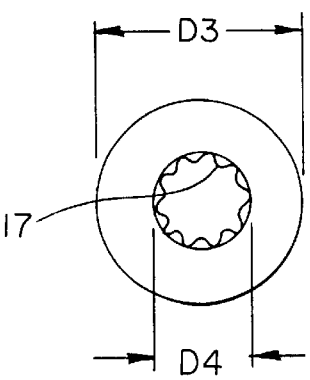
FIG. 15 is a schematic of a cross section of an IVD.

In FIG. 15 internal ribs are shown as typified by rib 17. Ribs in this location running the length of the interior lumen assist in releasing the IVD from the stylet. It may be convenient to extrude the IVD as a tube and then seal the end. This manufacturing technique is an alternative to molding the IVD as a single piece.

Figure 4:
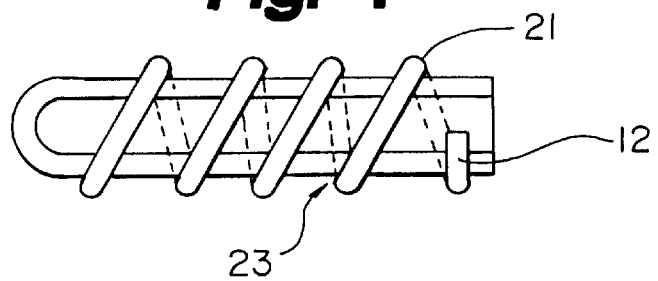
FIG. 4 is a cross section of an IVD.

FIG. 4 shows an IVD with a metallic coil 21 of copper or other metallic material encircling the outer portion of the IVD 23 device. The scale of the wire is exaggerated to show the preferred helical form. The helical form allows the IVD to stretch longitudinally. In general copper is known to be an effective spermacide when placed in the vas. The amount of metal must be predetermined to remain intact during the service life of the implanted IVD. It is generally know that metals have spermicidal attributes. The actual mechanisms for interfering with sperm are not well understood. It is believed that the placement of copper on the exterior of the IVD will result in a low toxicity highly effective male contraceptive.

Figure 5:
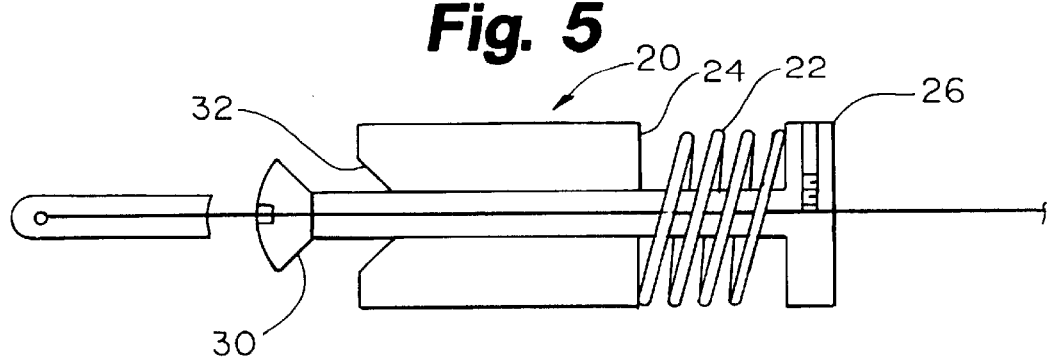
FIG. 5 is a cross section of an illustrative IVD delivery device

FIG. 5 shows a schematic cross section of a delivery device, which can be used to stretch the IVD into the operable position. The delivery device 20 has a spring 22 which supplies a force between a collar 24 and a collet closer member 26. In operation the tapered surface of the collet jaws 30 abuts and engages the tapered surface 32 of the collar 24. In this figure, a hand not seen, is forcing the spring 22 into compression by moving the collar 24 toward delivery device 20. In use the collar 24 forms a handle portion for the manipulation of the device. In use the physician will stretch the IVD toward the collet jaws 30 and release the handle to capture the proximal end surface of the IVD in the jaws. Or in the alternative the stylet 16 may be moved relative to the collet closer 26 by releasing the setscrew 17. In this mode the user would insert the proximal end of the IVD into the collet and allow the spring 22 to close the jaws around the IVD. Next the user would push the sytlet 6 into the IVD stretching it to the required length. Next the setscrew can be tightened to fix the stylet into the collet closer 26. This state is depicted in FIG. 6.

Figure 6:
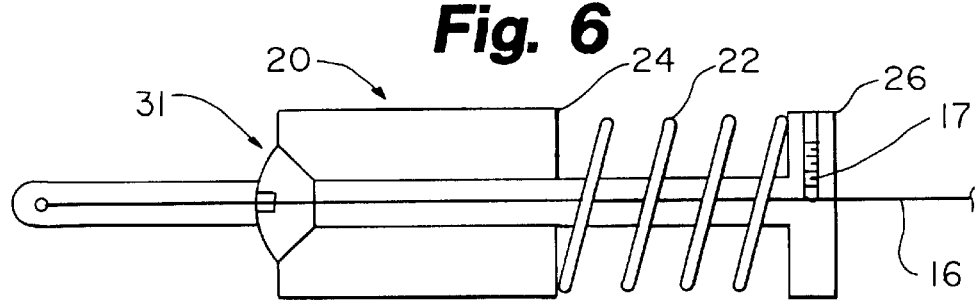
FIG. 6 is a cross section of an illustrative IVD delivery device.

FIG. 6 shows an IVD stretched and captured in the delivery device 20. In this state the spring 22 supplies traction to the IVD between the distal tip and the proximal surface. The amount of stretching is controlled by the length of the stylet 16. As described above the stylet 16 may be anchored in the collet closer member 26 with a setscrew 17 or the like to allow adjustment of the effective length of the stylet 16. In general the stylet is flexible yet stiff enough to resist buckling. The IVD and sytlet are easily manipulated by grasping and rotating the delivery device 20.

Figure 7:
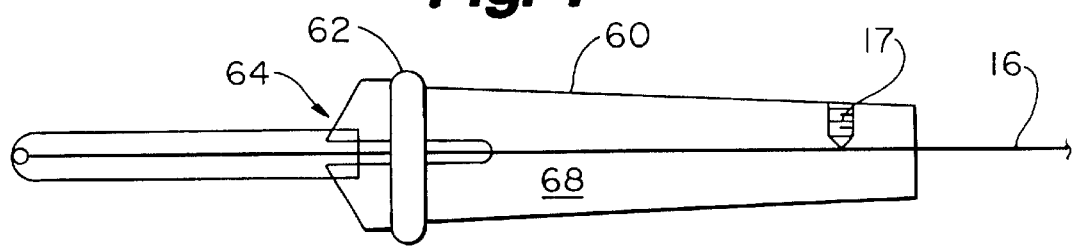
FIG. 7 is a cross section of an alternate IVD delivery device.

FIG. 7 is an alternate collet style IVD delivery device with a moveable ring 62 used to hold the collet jaws 64 in the closed position. In this device a setscrew 17 is used to retain and position the stylet 16 the handle 68.

Figure 8:
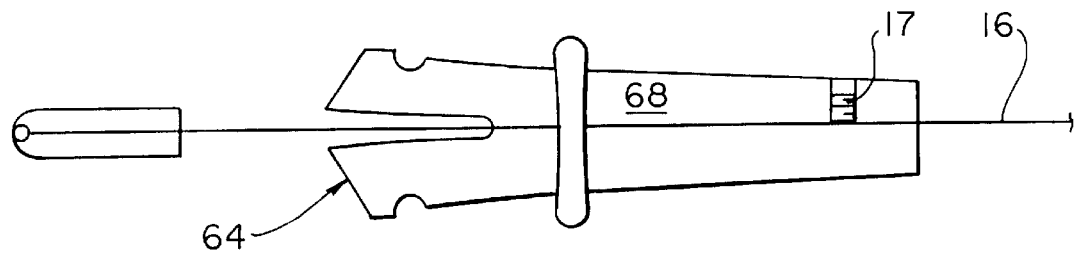
FIG. 8 is a cross section of an alternate IVD delivery device.

FIG. 8 is a view of the collet style IVD delivery device of FIG. 7 in the "open" position. In this view the ring 62 is forced proximal on the handle 68 to allow the collet to spring into the open position.

Figure 9:
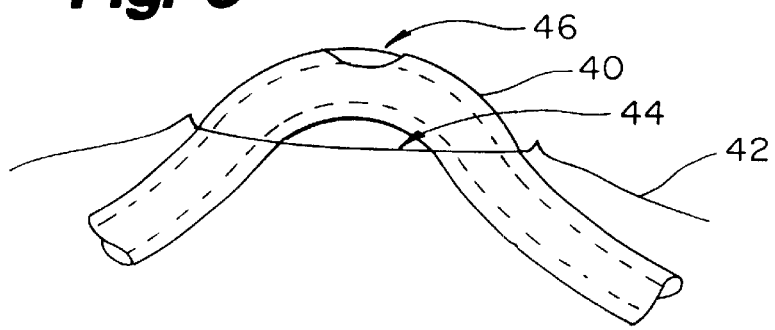
FIG. 9 is a schematic view of a step in a process.
Figure 10:
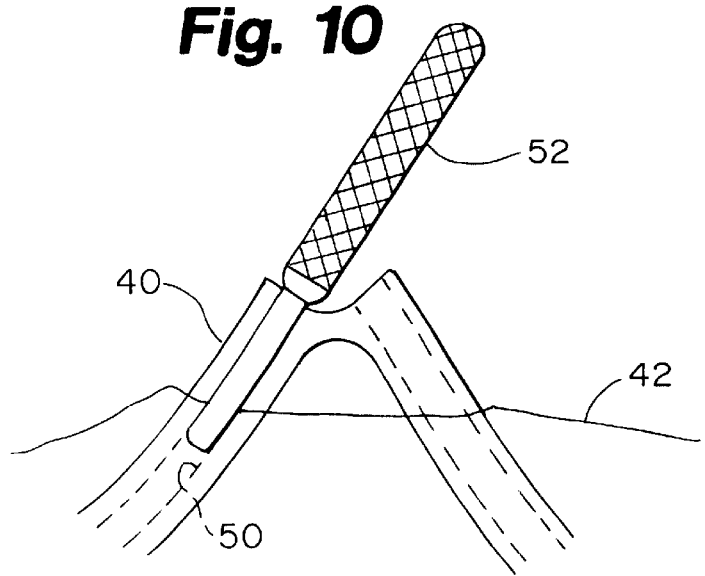
FIG. 10 is a schematic view of a step in a process.
Figure 11:
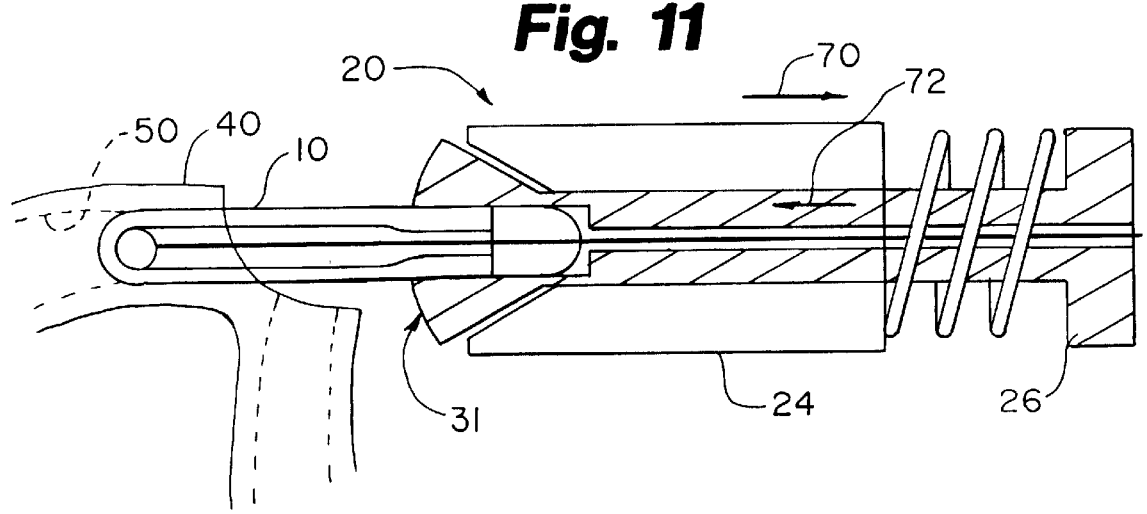
FIG. 11 is a schematic view of a step in a process.

FIGS. 9, 10 and 11, should be considered together. They are illustrative of a preferred and illustrative sequence for carrying out the method of the invention. In FIG. 9 the vas 40 is elevated above the scrotum 42 through an incision 44. A puncture incision 46 is made in the vas which does not completely sever the vas. In FIG. 10 the lumen 50 of the vas 40 is open and the lumen has a dilator/sizer 52 inserted into it. It has been found that the sooth muscle of the vas can contract and the size must be carefully determined to ensure a successful outcome. In FIG. 11 the delivery device 20 is positioned to release an IVD 10 in the lumen 50 vas 40. The fact that the diameter is reduced permits easier insertion in the vas with less trauma. With the IVD well placed the physician moves the collar 24 relative to the collet closer member 26 to release the IVD from the jaws 30. This motion is shown in the figure by arrows 70 and 72.

Figure 12:
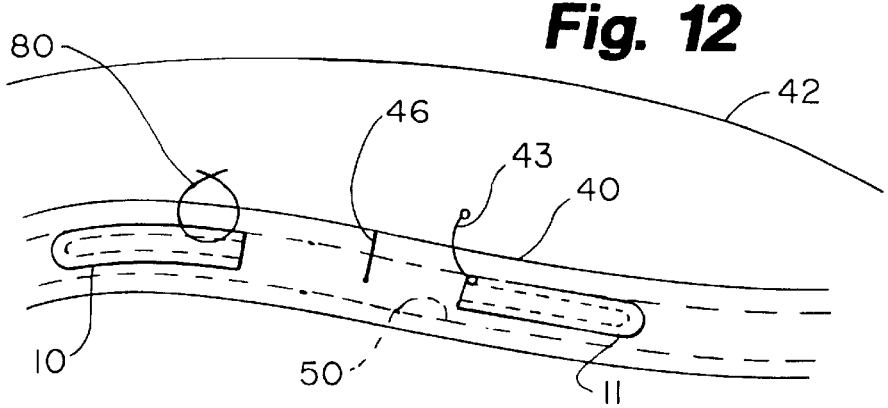
FIG. 12 is a schematic view of the completed procedure.

FIG. 12 shows a pair of opposed IVDs 10 and 11 respectively placed in a patient's vas 40. IVD 10 shows a suture loop 80 (exaggerated in the drawing for clarity) placed through the IVD 10 to secure it in a fixed location in the vas. IVD 11 has not been sutured but it includes a "tail" 43 seen in the figure as ball tethered to the main body of the IVD. The tail is left outside the vas and it is an optional feature of the IVD. The tail may take any of various forms including buttons or disks or rods. It is not clear which approach is best to prevent migration and both are permissible. IVD migration is not a primary concern if the sizer is used to select a near optimal size device.

One distinct advantage of the process and devices set forth above is that they may be surgically removed by reentry into the vas and removal of the IVD plugs. The suture 80 or "tail" 43 permit quick location of the location of the IVD devices. It is expected that the vas will heal with little scarring and the potency of the user returned. This reversibility is a major advantage of the device not shared with more invasive and destructive sterilization techniques.

Figure 13:
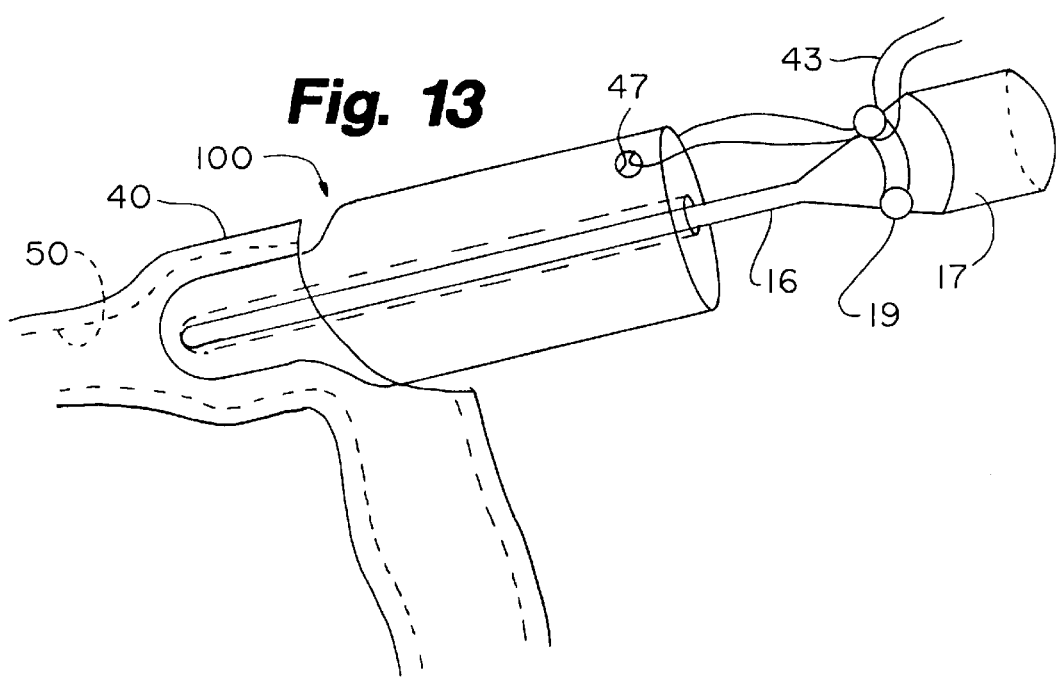
FIG. 13 is a schematic view of a step in a process.

FIG. 13 shows an alternate delivery strategy. This figure is similar to FIG. 11 where a device 10 is being inserted into the lumen 50 of a vas 40. The scale has been greatly exaggerated to depict the fact the vas is stretching during insertion. This stretching is shown by the bulging of the vas at location 100. At the same location the device 10 is being reduced in diameter during insertion. It is difficult to quantify the amount of vas stretching required for this method but the objective is to share or allocate the deformation required to fit the device between the device and the vas. It has been determined that this strategy results in a "tight" fit of the plug in the vas. It is anticipated that this amount of "tightness" will not cause tissue necrosis.

Device 10 insertion according to FIG. 13 can be accomplished with a stylet 16 alone or with a companion delivery tool which includes a handle 17 and an anchor to hold the device in the stretched condition if desired. The O-ring 19 depicted in the figure is an example of an anchor used to trap the tail 43.

In the alternative, if the device has a tail 43 attached the physician may press the tail or tether against the stylet 16 to hold the IVD in the stretched condition. The hole 47 may pierce the IVD off center or on center. Traction applied to the tether may be used to stretch the device.

This process is facilitated by the use of xylocane as a lubricant between the vas lumen 50 and the device 10. It is expected that other approved lubricants such as silicone or surface treatments on the device will also improve this insertion method. Xylocane is preferred because it is typically approved, available and used as an anesthetic for the procedure.

Figure 14:
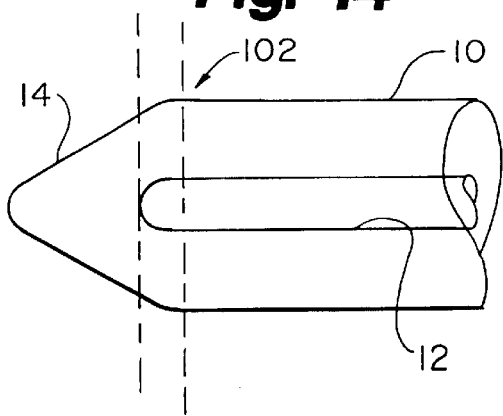
FIG. 14 is a schematic of a cross section of an IVD.

FIG. 14 shows a device 10 optimized for the insertion process. The blunt distal end 14 is slightly tapered rather than the hemispheric tip seen in other embodiments. This taper joins the cylindrical body of the device at location 102.

It is preferred to have the internal lumen terminate distal of location 102. This shape facilitates deformation of the device 10 by the vas during insertion and also reduces the occurrence of the stylet 16 from puncturing the device and the vas.

FIG. 15 shows the relative cross sections of the device diameter D3 and the interior lumen diameter D4. The device appears to work well with a nominal D3/D4 ratio of 1.75. Testing performed with deivces from 1.61 to 1.77 have proved workable.

It should be apparent that numerous modifications to the device or delivery tool may be made without departing from the scope of the invention, which is set forth in the claims.

What is claimed is:

1. A method of male contraception comprising the steps of: locating and exteriorizing and the vas;
    puncturing the vas exposing the vas lumen;
    selecting an intra vas device with a stretched diameter approximately equal to the vas lumen;
    stretching and holding the intra vas device to reduce its diameter;
    inserting the intra vas device in the vas lumen while the intra vas device is in the stretched condition;
    releasing the hold on the intra vas device allowing it to return to its nominal diameter while in the vas lumen.

2. The method of claim 1 wherein the selection step is preceded by:
    sizing the vas to select an IVD by inserting a sizer/dilator.

3. A delivery device for deploying an IVD of the type having an interior lumen and a distal end and a proximal end, said delivery device comprising:
    a stylet for insertion into said lumen of said IVD adapted to abut said distal end;
    a set of jaws for capturing the proximal end of said IVD;
    said jaws adapted to grasp said IVD in response to pressure applied to said jaws;
    a means for closing said jaws, positioned to supply traction between said stylet and said jaws, whereby said delivery device stretches said IVD a controlled amount;
    wherein said jaws are formed as a collet and said means for closing comprises a spring positioned between a collet closer and a collar;
    a release mechanism to release said jaws allowing said IVD to retract along the length of said stylet.

4. A delivery device for deploying an IVD of the type having an interior lumen and a distal end and a proximal end, said delivery device comprising:
    a stylet for insertion into said lumen of said IVD adapted to abut said distal end;
    a set of jaws for capturing the proximal end of said IVD;
    said jaws adapted to grasp said IVD in response to pressure applied to said jaws;
    a means for closing said jaws, positioned to supply traction between said stylet and said jaws, whereby said delivery device stretches said IVD a controlled amount;
    wherein said jaws are formed as a collet and said means for closing is a ring that when advanced distally closes and latches said jaws and when retracted proximally releases and opens said jaws;
    release mechanism to release said jaws allowing said IVD to retract along the length of said stylet.

5. An intra vas device (IVD) comprising:
    a tube having an outside diameter, made from a smooth soft compliant material and having a center lumen, and a first distal end which is closed and a second proximal end which is open.

6. The IVD of claim 5 wherein said ratio of said outside diameter to said inside lumen diameter is approximately 1.75.

7. The IVD of claim 6 wherein said compliant material is an elastomer.

8. The IVD of claim 5 further comprising a metallic element located on the outer surface of said IVD.

9. The IVD of claim 8 wherein said metallic element is a piece of copper wire surrounding said IVD outer surface.

10. The IVD of claim 8 wherein said metallic element is a coating of copper metal on the exterior surface of said IVD.

11. The IVD of claim 5 having an exterior surface formed as a series of ribs.

12. The IVD of claim 11 wherein said exterior surface has a coating of a metal.

13. An intra vas device (IVD) comprising:
    a tube having an outside diameter, made from a sooth soft compliant material and having a center lumen, and a first distal end which is closed and a second proximal end which is open, wherein said compliant material is an elastomer and wherein said elastomer is silicone rubber that has a durometer hardness of between about 20 and 40.

14. A system for male contraception comprising:
    an IVD plug to block the vas;
    a delivery device for grasping and stretching said IVD plug and for facilitating insertion of said IVD plug into the vas.

15. A method of male contraception comprising the steps of:
    locating and exteriorizing and the vas;
    puncturing the vas exposing the vas lumen;
    selecting an intra vas device;
    inserting the intra vas device in the vas lumen while the intra vas device is stretched by entry into the vas;
    releasing the hold on the intra vas device while allowing it to return to its nominal diameter in the vas lumen.

\* \* \* \* \*